(12) United States Patent
Ito et al.

(10) Patent No.: US 9,989,468 B2
(45) Date of Patent: Jun. 5, 2018

(54) FLUORESCENCE DETECTING APPARATUS

(71) Applicant: DISCO CORPORATION, Tokyo (JP)

(72) Inventors: Yusaku Ito, Tokyo (JP); Senichi Ryo, Tokyo (JP); Junichi Kuki, Tokyo (JP)

(73) Assignee: Disco Corporation, Tokyo (JP)

(*) Notice: Subject to any disclaimer, the term of this patent is extended or adjusted under 35 U.S.C. 154(b) by 0 days. days.

(21) Appl. No.: 15/621,197

(22) Filed: Jun. 13, 2017

(65) Prior Publication Data
US 2017/0370845 A1    Dec. 28, 2017

(30) Foreign Application Priority Data
Jun. 22, 2016 (JP) ................... 2016-123697

(51) Int. Cl.
*G01N 21/64* (2006.01)

(52) U.S. Cl.
CPC . *G01N 21/6456* (2013.01); *G01N 2021/6471* (2013.01)

(58) Field of Classification Search
CPC .......... G01N 21/64; G01N 2021/6495; G01N 21/6456; G01N 2021/6471
See application file for complete search history.

(56) References Cited

U.S. PATENT DOCUMENTS 4,841,156 A * 6/1989 May ................... G01B 11/0658
250/459.1
2002/0127950 A1* 9/2002 Hirose ................. B24B 37/013
451/6

FOREIGN PATENT DOCUMENTS

JP    2012-104532    5/2012

* cited by examiner

*Primary Examiner* — David Porta
*Assistant Examiner* — Faye Boosalis
(74) *Attorney, Agent, or Firm* — Greer Burns & Crain Ltd.

(57) ABSTRACT

A fluorescence detecting apparatus includes an excitation light applying section that applies excitation light to a protective film containing an absorbing agent. A photomultiplier tube detects fluorescence emitted from the absorbing agent due to absorption of the excitation light. A fluorescence passing filter removes light having wavelengths other than the wavelength of the fluorescence emitted from the absorbing agent, and a reflecting mirror having a reflecting surface reflects the fluorescence emitted from the protective film toward the photomultiplier tube. This reflecting surface is formed by a part of a curved surface forming a spheroid having first and second foci. The first focus is positioned at a target area of the protective film where the excitation light is applied, and the second focus is positioned at a light detecting element included in the photomultiplier tube.

5 Claims, 10 Drawing Sheets

FLUORESCENCE DETECTING APPARATUS

BACKGROUND OF THE INVENTION

Field of the Invention

The present invention relates to a fluorescence detecting apparatus for detecting fluorescence emitted from a protective film formed on a workpiece.

Description of the Related Art

In the case of performing laser processing to a wafer as a workpiece, a laser beam is applied to the wafer in the condition where a protective film is formed on the wafer in an area where devices are formed. By forming the protective film, it is possible to prevent processing dust such as debris generated in performing the laser processing from directly adhering to the front side of each device, thereby well processing the wafer. In such a conventional laser processing method, an absorbing agent capable of absorbing the laser beam for processing the wafer is contained in the protective film thereby to make the laser processing efficient. Further, the absorbing agent has a property of emitting fluorescence in absorbing light having a wavelength near the wavelength of the laser beam for processing the wafer, and there has been proposed a technique of detecting the intensity of the fluorescence emitted from the protective film containing the absorbing agent, thereby detecting the formed condition of the protective film (see Japanese Patent Laid-open No. 2012-104532, for example).

SUMMARY OF THE INVENTION

However, the fluorescence emitted from the absorbing agent contained in the protective film is isotropic and feeble light. Accordingly, it is difficult to detect the formed condition of the protective film with high accuracy.

It is therefore an object of the present invention to provide a fluorescence detecting apparatus which can efficiently obtain the intensity of fluorescence emitted from a protective film to thereby detect the formed condition of the protective film with high accuracy.

In accordance with an aspect of the present invention, there is provided a fluorescence detecting apparatus for detecting whether or not a protective film is properly formed on the front side of a workpiece, by using fluorescence emitted from the protective film, the protective film being formed to protect the front side of the workpiece from processing dust generated in applying a laser beam to the front side of the workpiece to process the workpiece, the protective film being formed of a resin containing an absorbing agent capable of absorbing the laser beam, the fluorescence detecting apparatus including a holding section configured to hold the workpiece; and light detecting means for detecting the fluorescence emitted from the protective film to thereby detect the formed condition of the protective film; the light detecting means including an excitation light applying section configured to apply excitation light to the protective film, the excitation light having an absorption wavelength to the absorbing agent contained in the protective film, a light detecting section configured to detect the fluorescence emitted from the absorbing agent due to the absorption of the excitation light, a filter for removing light having wavelengths other than the wavelength of the fluorescence emitted from the absorbing agent, and a reflecting mirror having a reflecting surface for reflecting the fluorescence emitted from the protective film toward the light detecting section; the reflecting surface being formed by a part of a curved surface forming a spheroid having two foci, one of the two foci being positioned at a target area of the protective film where the excitation light is applied, whereas the other focus being positioned at the light detecting section.

With this configuration, the fluorescence emitted from the absorbing agent contained in the protective film at one of the two foci of the spheroid is reflected on the reflecting surface formed as a part of the curved surface of the spheroid. Accordingly, the fluorescence reflected from the reflecting mirror can be efficiently guided to the light detecting section positioned at the other focus of the spheroid. As a result, the formed condition of the protective film can be detected with high accuracy according to the fluorescence detected by the light detecting section.

Preferably, the light detecting section includes a photomultiplier tube. Preferably, the excitation light applying section is provided between the target area of the protective film and the filter. Preferably, the holding section is used also in performing laser processing to the workpiece. Preferably, the light detecting means further includes a casing for storing all the excitation light applying section, the light detecting section, the filter, and the reflecting mirror.

As another aspect of the present invention, the light detecting means includes a light detecting section configured to detect the fluorescence, a filter for removing light having wavelengths other than the wavelength of the fluorescence, a casing for storing the light detecting section and the filter, and a reflecting mirror having a reflecting surface for reflecting the fluorescence emitted from a predetermined position (protective film) outside the casing and entered the casing toward the light detecting section, wherein the reflecting surface is formed by a part of a curved surface forming a spheroid having a first focus and a second focus. The first focus of the spheroid is positioned in the light detecting section. The casing is vertically movable so that the second focus is positioned on a predetermined target member (protective film) to be detected.

With this configuration, the fluorescence emitted from the absorbing agent contained in the protective film at the second focus of the spheroid is reflected on the reflecting surface formed as a part of the curved surface of the spheroid. Accordingly, the fluorescence reflected from the reflecting mirror can be efficiently guided to the light detecting section positioned at the first focus of the spheroid. As a result, the formed condition of the protective film can be detected with high accuracy according to the fluorescence detected by the light detecting section.

The above and other objects, features and advantages of the present invention and the manner of realizing them will become more apparent, and the invention itself will best be understood from a study of the following description and appended claims with reference to the attached drawings showing a preferred embodiment of the invention.

DETAILED DESCRIPTION OF THE PREFERRED EMBODIMENT

A preferred embodiment of the present invention will now be described in detail with reference to the drawings. The present invention is not limited to this preferred embodiment. Further, the components used in this preferred embodiment may include those that can be easily assumed by persons skilled in the art or substantially the same elements as those known in the art. Further, the configurations described below may be suitably combined. Further, the configurations may be variously omitted, replaced, or changed without departing from the scope of the present invention.

Figure 1:
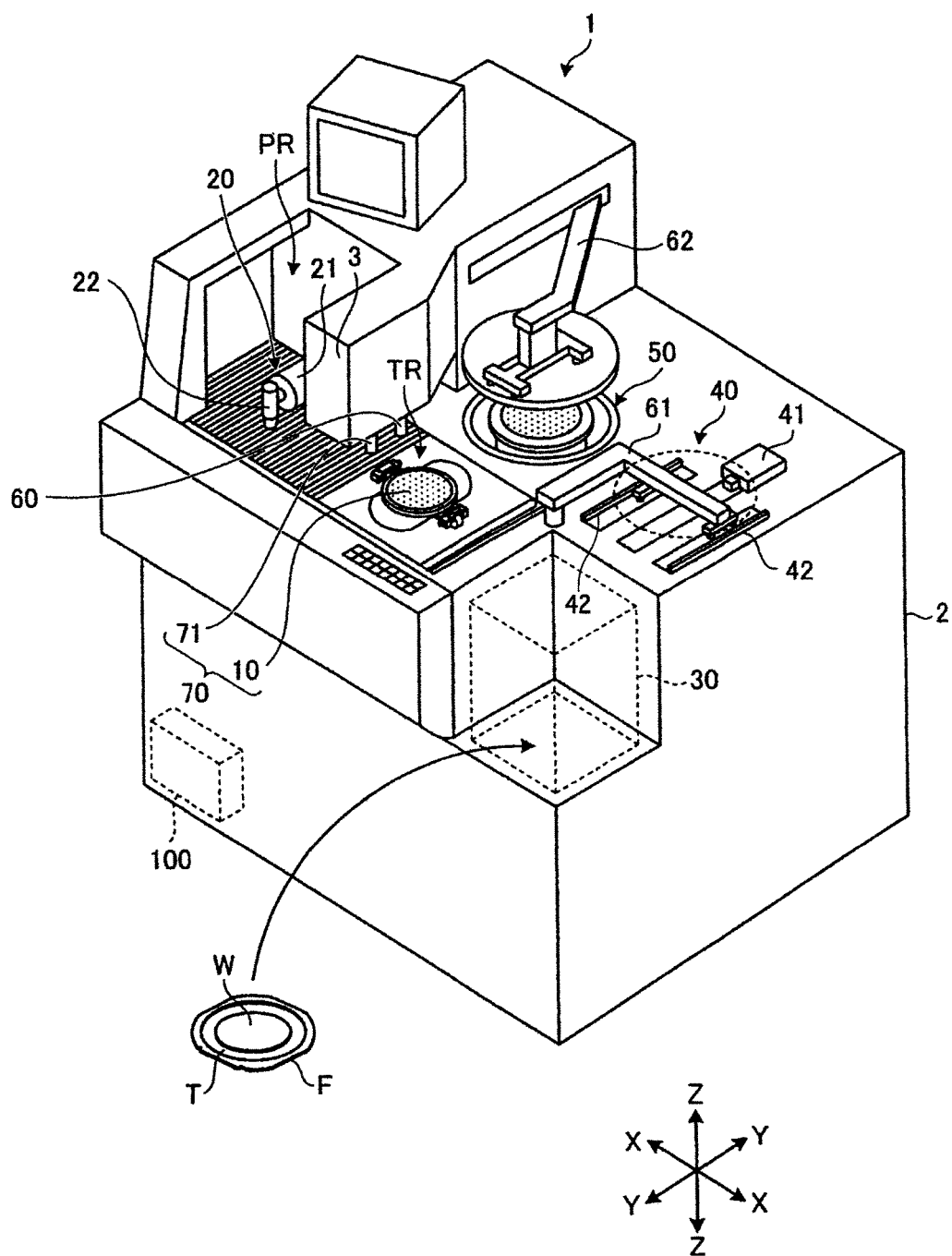
FIG. 1 is a perspective view of a laser processing apparatus including a fluorescence detecting apparatus according to a preferred embodiment of the present invention.
Figure 2:
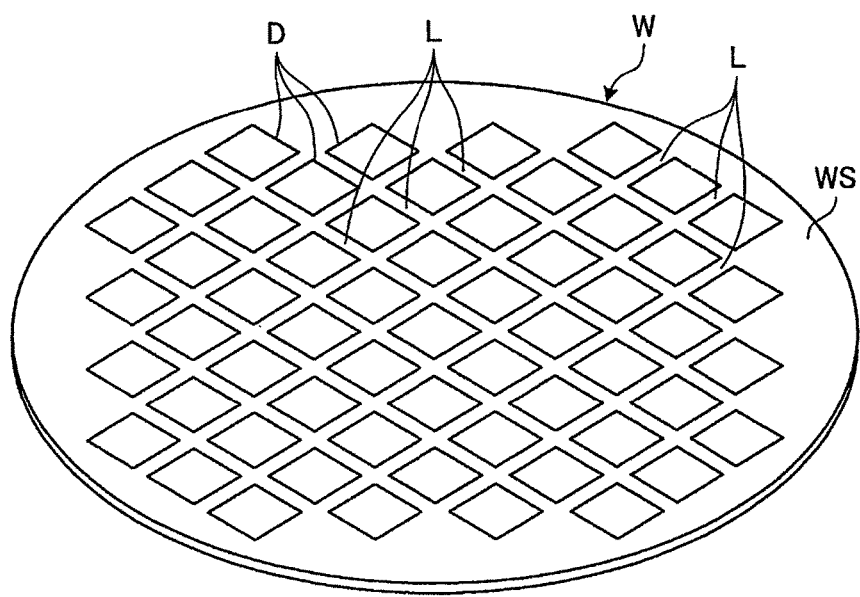
FIG. 2 is a perspective view of a wafer as a workpiece to be processed by the laser processing apparatus.
Figure 3:
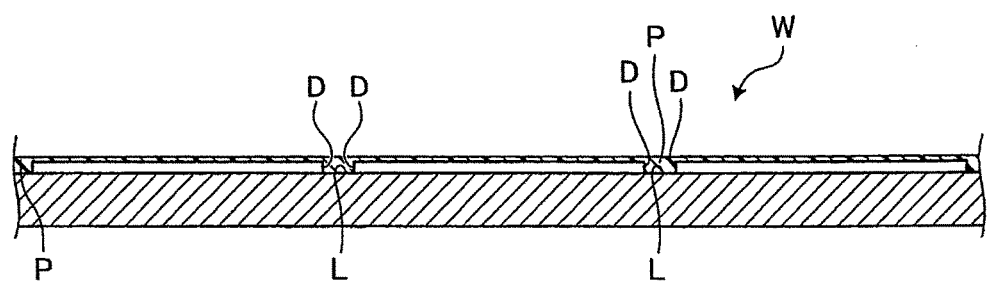
FIG. 3 is a sectional view of the wafer in the condition where a protective film is formed on the front side of the wafer.

FIG. 1 is a perspective view of a laser processing apparatus 1 including a fluorescence detecting apparatus 70 according to this preferred embodiment. FIG. 2 is a perspective view of a wafer W as a workpiece to be processed by the laser processing apparatus 1. FIG. 3 is a sectional view of the wafer W in the condition where a protective film P is formed on the front side of the wafer W. The wafer W to be processed by the laser processing apparatus 1 shown in FIG. 1 is a semiconductor wafer or an optical device wafer having a disk-shaped substrate WS as shown in FIG. 2. The substrate WS of the wafer W is formed of silicon, sapphire, or gallium arsenide, for example. As shown in FIG. 2, a plurality of crossing streets (target lines) L to be processed are formed on the front side (work surface) of the substrate WS (wafer W) to thereby define a plurality of separate regions where a plurality of devices D are formed. The laser processing apparatus 1 functions to apply a laser beam along the streets L of the wafer W, thereby forming a laser processed groove along each street L (laser processing). As shown in FIG. 3, the protective film P for essentially covering the streets L is formed on the front side of the wafer W, so as to prevent that debris (processing dust) generated in performing the laser processing may adhere to the front side of the wafer W, i.e., to the front side of each device D.

After performing the laser processing, this protective film P is removed from the front side of the wafer W by any means such as cleaning means.

As shown in FIG. 1, the laser processing apparatus 1 includes a chuck table (holding section) 10 and a laser beam applying section 20. The laser processing apparatus 1 further includes a cassette elevator (not shown) on which a cassette 30 for storing a plurality of wafers W before or after laser processing is adapted to be placed. A temporary setting section 40 is provided on the rear side of the cassette 30 placed on the cassette elevator to temporarily set the wafer W before or after laser processing. The laser processing apparatus 1 further includes a coating and cleaning section 50 for forming the protective film P on the wafer W before laser processing and for removing the protective film P from the wafer W after laser processing and an imaging section 60 for imaging the wafer W held on the chuck table 10.

The laser processing apparatus 1 further includes the fluorescence detecting apparatus 70 for detecting the formed condition (presence or absence) of the protective film P formed on the front side of the wafer W. The fluorescence detecting apparatus 70 includes a fluorescence detecting unit (light detecting means) 71 and the chuck table 10. The fluorescence detecting unit 71 is located adjacent to the imaging section 60. Both the fluorescence detecting unit 71 and the imaging section 60 are mounted on a support portion 3 of a body (base) 2 constituting the laser processing apparatus 1. The support portion 3 is so formed as to extend above a moving path of the chuck table 10.

The laser processing apparatus 1 further includes X moving means (not shown) for relatively moving the chuck table 10 and the laser beam applying section 20 in the X direction shown by an arrow X, Y moving means (not shown) for relatively moving the chuck table 10 and the laser beam applying section 20 in the Y direction shown by an arrow Y, and Z moving means (not shown) for relatively moving the chuck table 10 and the laser beam applying section 20 in the Z direction shown by an arrow Z. The laser processing apparatus 1 further includes a control section 100 built in the body 2 for controlling the operation of each component of the laser processing apparatus 1.

The chuck table 10 functions to hold the wafer W in performing laser processing to the wafer W in the condition where the protective film P is formed on the wafer W. The chuck table 10 has a disk-shaped upper surface portion (vacuum chuck) formed of porous ceramic, for example. This upper surface portion of the chuck table 10 is connected through a vacuum line (not shown) to a vacuum source (not shown). Accordingly, this upper surface portion of the chuck table 10 functions to suck the back side of the wafer W placed on the chuck table 10, thereby holding the wafer W under suction. The chuck table 10 is movable in the X direction by the X moving means between a standby position TR near the cassette 30 where the wafer W is loaded/unloaded with respect to the chuck table 10 and a working position PR near the laser beam applying section 20 where the wafer W is processed by a laser beam. The chuck table 10 is also movable in the Y direction by the Y moving means. The chuck table 10 is rotatable around a vertical axis extending in the Z direction by a pulse motor (rotating mechanism) (not shown). In this preferred embodiment, the chuck table 10 is rotatable at a predetermined speed (e.g., 3000 rpm) under the control of the control section 100.

The laser beam applying section 20 is located above the working position PR and functions to apply a laser beam to the front side of the wafer W held on the chuck table 10, thereby forming a laser processed groove along each street L. The laser beam has an absorption wavelength to the wafer W. The laser beam applying section 20 is movable in the Z direction by the Z moving means with respect to the wafer W held on the chuck table 10. The laser beam applying section 20 includes oscillating means 21 for oscillating a laser beam and focusing means 22 for focusing the laser beam oscillated by the oscillating means 21. In the oscillating means 21, the frequency of the laser beam to be oscillated is suitably adjusted according to the kind of the wafer W, the form of processing, etc. The oscillating means 21 includes a laser oscillator such as a YAG (yttrium aluminum garnet) laser oscillator and a YVO4 (yttrium vanadate) laser oscillator. The focusing means 22 includes a total reflection mirror for changing the traveling direction of the laser beam oscillated by the oscillating means 21 and a focusing lens for focusing the laser beam reflected by the total reflection mirror.

The cassette 30 is so configured as to store a plurality of wafers W in the condition where each wafer W is attached through an adhesive tape T to an annular frame F as shown in FIG. 1. The cassette elevator is provided in the body 2 of the laser processing apparatus 1 so as to be vertically movable in the Z direction.

The temporary setting section 40 functions to temporarily set one of the plural wafers W taken out of the cassette 30 before laser processing and also temporarily set the wafer W after laser processing. More specifically, the temporary setting section 40 includes handling means 41 for taking one of the plural wafers W out of the cassette 30 before laser processing and also for returning the wafer W into the cassette 30 after laser processing and a pair of rails 42 for temporarily positioning the wafer W handled by the handling means 41 before or after laser processing.

The laser processing apparatus 1 further includes first transfer means 61 and second transfer means 62. The first transfer means 61 functions to transfer the wafer W from the pair of rails 42 to the coating and cleaning section 50 before laser processing, wherein the protective film P is formed on the wafer W in the coating and cleaning section 50. The second transfer means 62 functions to transfer the wafer W from the chuck table 10 to the coating and cleaning section 50 after laser processing, wherein the protective film P is removed from the wafer W in the coating and cleaning section 50. Each of the first and second transfer means 61 and 62 is so configured as to hold the front side of the wafer W under suction and then lift the wafer W while transferring it to a desired position.

Figure 4:
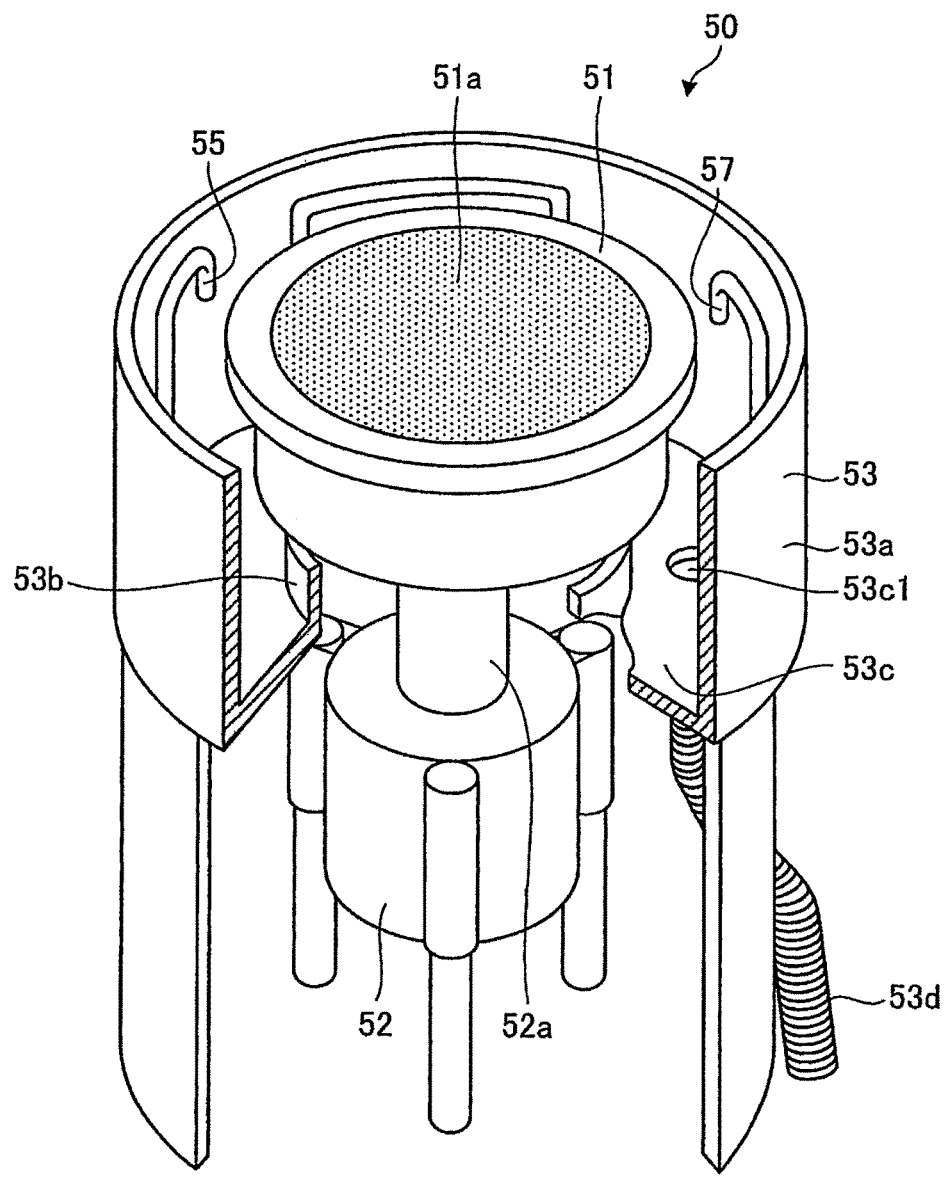
FIG. 4 is a perspective view showing the configuration of a coating and cleaning section included in the laser processing apparatus.

FIG. 4 is a perspective view showing the configuration of the coating and cleaning section 50. As shown in FIG. 4, the coating and cleaning section 50 includes a spinner table (holding section) 51 for holding the wafer W before or after laser processing, an electric motor 52 for rotating the spinner table 51 around a vertical axis extending in the Z direction (see FIG. 1), and a liquid receiving section 53 provided so as to surround the spinner table 51. The spinner table 51 includes a disk-shaped vacuum chuck 51a formed at a central portion of the upper surface. The vacuum chuck 51a is formed of porous ceramic, for example, and it is in communication with suction means (not shown). Accordingly, the wafer W placed on the vacuum chuck 51a of the spinner table 51 can be held under suction.

The electric motor 52 has a drive shaft 52a, and the spinner table 51 is connected to the upper end of the drive shaft 52a. The electric motor 52 is so configured as to rotatably support the spinner table 51. The rotational speed of the electric motor 52 is controlled by the control section 100. Accordingly, the electric motor 52 is operated at a predetermined rotational speed (e.g., 3000 rpm) under the control of the control section 100. The liquid receiving section 53 is annularly formed in such a manner that it is composed of a cylindrical outer wall 53a, a cylindrical inner wall 53b, and a bottom wall 53c connecting the outer wall 53a and the inner wall 53b. The liquid receiving section 53 functions to receive a liquid resin supplied to the front side of the wafer W in forming the protective film P and also to receive a cleaning water supplied to the front side of the wafer W in removing the protective film P. The bottom wall 53c is formed with a drain opening 53c1, and a drain hose 53d is connected to the drain opening 53c1.

The coating and cleaning section 50 further includes a liquid resin nozzle 55 and a cleaning water nozzle 57. The liquid resin nozzle 55 functions to supply a water-soluble liquid resin to the wafer W held on the spinner table 51 before laser processing, wherein the water-soluble liquid resin is applied to the front side of the wafer W to form the protective film P. The cleaning water nozzle 57 functions to supply a cleaning water to the wafer W held on the spinner table 51 after laser processing, thereby removing the protective film P. Each of the nozzles 55 and 57 has a nozzle opening movable between a working position above the center of the spinner table 51 and a retracted position outside the outer circumference of the spinner table 51. The liquid resin nozzle 55 is connected to a liquid resin source (not shown), so that the water-soluble liquid resin can be supplied from the liquid resin source through the liquid resin nozzle 55 to the front side of the wafer W.

Examples of the water-soluble liquid resin include PVA (polyvinyl alcohol), PEG (polyethylene glycol), PVP (polyvinyl pyrrolidone), polyethylene oxide, polyethylene imine, carboxy methyl cellulose, and hydroxy ethyl cellulose. The liquid resin to be used has a viscosity of 20 to 400 cp. The liquid resin in the present invention contains an absorbing agent for assisting the absorption of the laser beam. Examples of such an absorbing agent include 4,4'-dicarboxy benzophenone, benzophenone-4-caboxylic acid, 2-carboxy anthraquinone, 1,2-naphthalene dicarboxylic acid, 1,8-naphthalene dicarboxylic acid, 2,3-naphthalene dicarboxylic acid, 2,6-naphthalene dicarboxylic acid, 2,7-naphthalene dicarboxylic acid, sodium salt, potassium salt, ammonium salt, quaternary ammonium salt of these acids, sodium salt of 2,6-anthraquinone disulfonic acid, sodium salt of 2,7-anthraquinone disulfonic acid, and ferulic acid. The absorbing agent may be dissolved in the liquid resin in actual use. In the case that the laser beam has a wavelength of 355 nm, ferulic acid is preferably used as the absorbing agent.

In place of such an organic compound including ferulic acid or in addition thereto, fine particles of oxide capable of accelerating the laser processing in an ultraviolet region may be added by an amount of 0.1 to 10 vol. % to the liquid resin. In this case, the fine particles of oxide are dispersed in the liquid resin. Examples of the oxide forming the fine particles include $TiO_2$, $ZnO$, $Fe_2O_3$, $CeO_2$, $CuO$, $Cu_2O$, $MgO$, and $SiO_2$. The liquid resin applied to the front side of the wafer W is solidified by drying, thereby forming the protective film P (FIG. 3) for protecting the front side of the wafer W. The cleaning water nozzle 57 is connected to a cleaning water source (not shown), so that a cleaning water (e.g., pure water) can be supplied from the cleaning water source through the cleaning water nozzle 57 to the front side of the wafer W, thereby removing the protective film P from the front side of the wafer W after laser processing.

The imaging section 60 includes an optical system such as a microscope and an imaging device such as CCD (charge-coupled device). An image signal obtained by the imaging section 60 is transmitted to the control section 100. The control section 100 performs alignment in such a manner as to rotate the chuck table 10 by driving the associated pulse motor according to the image signal received from the imaging section 60 and thereby to make the streets L extending in a first direction on the wafer W held on the chuck table 10 parallel to the processing direction (X direction). Accordingly, the other streets L extending in a second direction perpendicular to the first direction becomes parallel to the Y direction.

Figure 5:
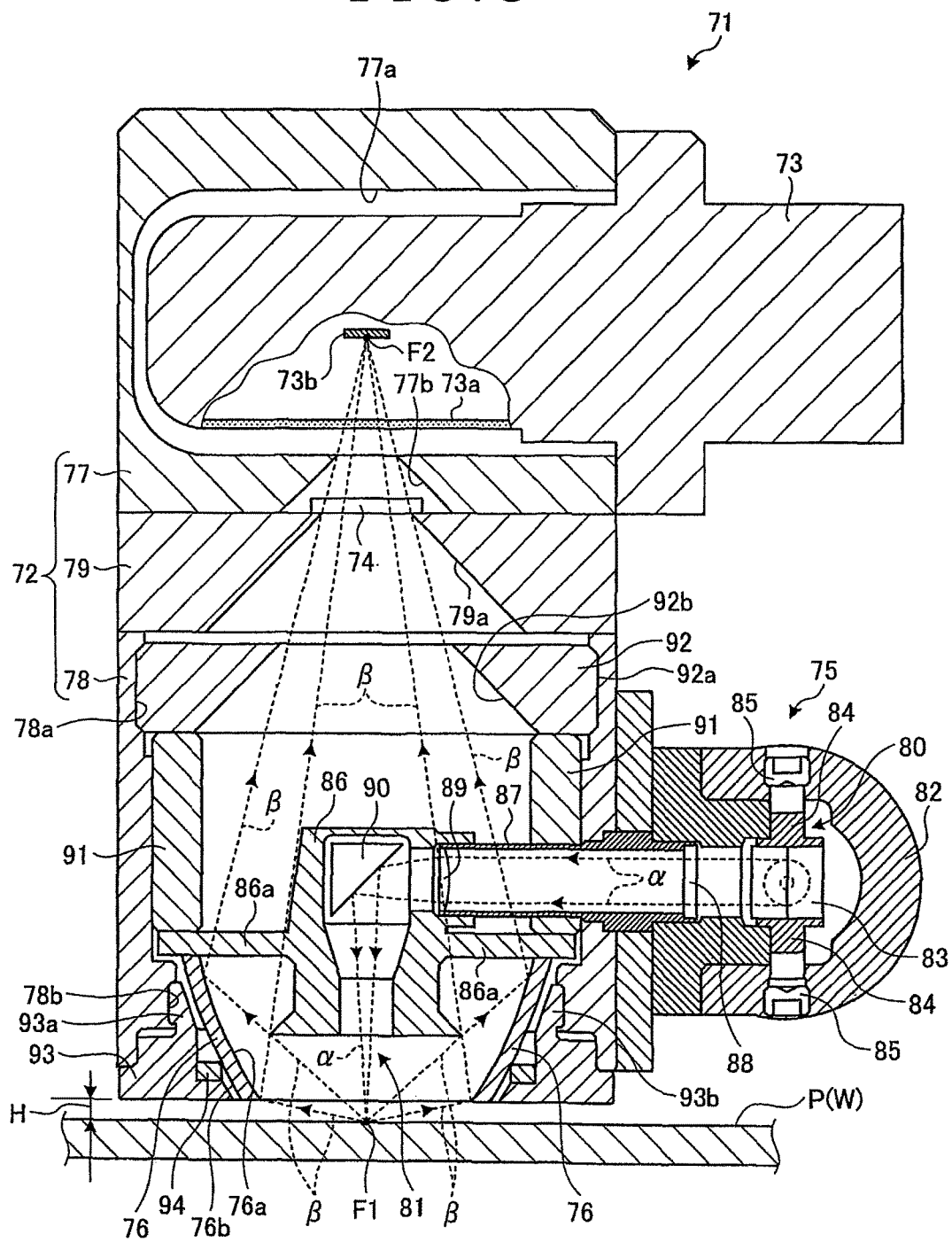
FIG. 5 is a vertical sectional view showing the internal configuration of a fluorescence detecting unit included in the laser processing apparatus.

The fluorescence detecting unit 71 will now be described. FIG. 5 is a sectional view showing the internal configuration of the fluorescence detecting unit 71. The fluorescence detecting unit 71 functions to apply excitation light α having a wavelength (e.g., 365 nm) different from the processing wavelength (e.g., 355 nm) of the laser beam to the protective film P and then detect the intensity of fluorescence β (having a wavelength of 420 to 430 nm, for example) emitted from the absorbing agent contained in the protective film P due to absorption of the excitation light α. Information on the intensity of the fluorescence β detected by the fluorescence detecting unit 71 is transmitted to the control section 100. Then, the control section 100 determines the formed condition (presence or absence) of the protective film P on the wafer W.

As shown in FIG. 5, the fluorescence detecting unit 71 includes a casing 72, a photomultiplier tube (light detecting section) 73, a fluorescence passing filter (filter) 74, an excitation light applying section 75, and a reflecting mirror 76, wherein all of the components 73, 74, 75, and 76 are mounted to the casing 72. The casing 72 forms the outside shape of the fluorescence detecting unit 71. The casing 72 is composed of a tube fixing member 77, a mirror fixing member 78, and a connecting member 79 for connecting the tube fixing member 77 and the mirror fixing member 78, wherein these members 77, 78, and 79 are stacked in the Z direction (vertical direction). The tube fixing member 77 is located at the upper portion of the casing 72 and has an internal space 77a for receiving the photomultiplier tube 73. That is, the photomultiplier tube 73 is partially inserted in the internal space 77a of the tube fixing member 77 from a side surface thereof. The tube fixing member 77 has a lower portion opposed to the connecting member 79. The lower portion of the tube fixing member 77 is formed with a first opening 77b communicating with the internal space 77a. The first opening 77b is formed at the center of the lower portion of the tube fixing member 77 and has a diameter gradually increased toward the connecting member 79.

The photomultiplier tube 73 is a highly sensitive photodetector having a function of converting optical energy into electrical energy by utilizing a photoelectric effect and also having a function of electric current amplification (electron multiplication). The photomultiplier tube 73 includes a glass tube 73a for defining a vacuum region and a light detecting element 73b provided in this vacuum region for detecting photoelectrons (photons). The light detecting element 73b is adapted to detect the photoelectrons of the fluorescence β passed through the glass tube 73a. The photoelectrons detected collide with each other to sequentially produce secondary electrons and thereby amplify an electric current. In this preferred embodiment, a model R9110P manufactured by Hamamatsu Photonics K. K. is adopted as the photomultiplier tube 73.

The connecting member 79 has a second opening 79a communicating with the first opening 77b of the tube fixing member 77. As similar to the first opening 77b, the second opening 79a has a diameter gradually increased toward the mirror fixing member 78. The upper end of the second opening 79a is smaller in diameter than the lower end of the first opening 77b. The fluorescence passing filter 74 is located on the upper surface of the connecting member 79 so as to cover the upper end of the second opening 79a. The fluorescence passing filter 74 functions to pass only the fluorescence β emitted from the absorbing agent and accordingly remove light having wavelengths other than the wavelength of the fluorescence β. Accordingly, even when a part of the excitation light α scatters to enter the second opening 79a, the excitation light α scattered can be removed by the fluorescence passing filter 74.

The mirror fixing member 78 is a cylindrical member, in which a part of the excitation light applying section 75 and the reflecting mirror 76 are fixed. The excitation light applying section 75 functions to apply excitation light α having an absorption wavelength (e.g., 365 nm) to the absorbing agent contained in the protective film P, toward a target area on the protective film P. The excitation light applying section 75 includes an LED (light-emitting diode) (not shown) as a light source provided outside the casing 72, a first light guiding section 80 for guiding the excitation light α emitted from the LED to the inside of the casing 72, and a second light guiding section 81 for guiding the excitation light α guided into the casing 72 by the first light guiding section 80, toward the protective film P. The first light guiding section 80 has a first mirror holding member 82 fixed to the outer circumferential surface of the mirror fixing member 78. A first mirror 83 is provided inside the first mirror holding member 82, so as to reflect the excitation light α emitted from the back side of the sheet plane of FIG. 5 and then guide the excitation light α into the mirror fixing member 78 (the casing 72). The upper and lower surfaces of the first mirror 83 are held by a pair of holding members 84. An operating screw 85 is connected to each holding member 84, wherein the operating screw 85 is rotated to thereby allow the rotation of the first mirror 83 around the axis of the operating screw 85.

The second light guiding section 81 includes a second mirror holding member 86 fixed in the mirror fixing member 78 and a light guide pipe 87 for connecting the second mirror holding member 86 and the first mirror holding member 82. An excitation light passing filter 88 is provided at the inlet of the light guide pipe 87, and a focusing lens 89 is provided at the outlet of the light guide pipe 87. A second mirror 90 is provided inside the second mirror holding member 86, so as to reflect the excitation light α passed through the focusing lens 89 and then guide the excitation light α to the protective film P. Although not shown, the opposite side surfaces of the second mirror 90 as viewed in the direction perpendicular to the sheet plane of FIG. 5 are held by a pair of holding members. An operating screw is connected to each holding member, wherein this operating screw is rotated to thereby allow the rotation of the second mirror 90 around the axis of this operating screw. With this arrangement, the first mirror 83 and the second mirror 90 can be adjusted in angle to thereby allow the adjustment of a spot position of the excitation light α to be applied to the protective film P.

The second mirror holding member 86 is located between the fluorescence passing filter 74 and the target area on the protective film P. With this arrangement, the excitation light α applied through the second mirror holding member 86 to the protective film P can be reliably removed by the fluorescence passing filter 74. The second mirror holding member 86 has an outer circumferential surface from which a plurality of (e.g., four) arm portions 86a project radially outward. These arm portions 86a are sandwiched between the reflecting mirror 76 and a spacer 91 provided inside the mirror fixing member 78, whereby the second mirror holding member 86 is fixed inside the mirror fixing member 78. A positioning ring 92 is provided in the mirror fixing member 78 at an upper portion thereof so as to be fitted to the inner surface thereof. More specifically, an external thread portion 92a is formed on the outer circumferential surface of the positioning ring 92, and an internal thread portion 78a is formed on the inner surface of the mirror fixing member 78, wherein the external thread portion 92a of the positioning ring 92 is engaged with the internal thread portion 78a of the mirror fixing member 78. By thus mounting the positioning ring 92 in the mirror fixing member 78, the height (vertical position) of the positioning ring 92 in the mirror fixing member 78 is determined, so that the height (vertical position) of the spacer 91 abutting against the positioning ring 92 is also determined. The positioning ring 92 has a tapering inner circumferential surface 92b, which is increased in diameter toward the spacer 91 as similar to the first opening 77b and the second opening 79a. That is, the inner circumferential surface 92b of the positioning ring 92 forms a tapered opening similar to the first opening 77b and the second opening 79a. The upper end of this tapered opening formed by the inner circumferential surface 92b is smaller in diameter than the lower end of the second opening 79a.

Further, a mirror supporting member 93 for supporting the reflecting mirror 76 is mounted on the inner surface of the mirror fixing member 78 at a lower portion thereof. The mirror supporting member 93 has a cylindrical portion 93a extending upward, wherein an external thread portion 93b is formed on the outer circumferential surface of the cylindrical portion 93a. On the other hand, an internal thread portion 78b is formed on the inner surface of the lower portion of the mirror fixing member 78. The external thread portion 93b of the mirror supporting member 93 is engaged with the internal thread portion 78b of the mirror fixing member 78. By tightening the external thread portion 93b of the mirror supporting member 93 with respect to the internal thread portion 78b of the mirror fixing member 78, the mirror supporting member 93 is vertically moved relative to the mirror fixing member 78. Accordingly, a compression rubber ring 94 provided on the inner surface of the mirror supporting member 93 abuts against the outer circumferential surface 76b of the reflecting mirror 76 and pushes it upward in a compressed condition. As a result, the arm portions 86a of the second mirror holding member 86 are firmly held between the upper end of the reflecting mirror 76 and the lower end of the spacer 91, so that the second mirror holding member 86 is fixed inside the mirror fixing member 78.

In the condition where the reflecting mirror 76 is mounted in the casing 72, the outer diameter of the reflecting mirror 76 substantially coincides with the inner diameter of the compression rubber ring 94 set on the mirror supporting member 93. The reflecting mirror 76 is supported directly or through the compression rubber ring 94 to the mirror supporting member 93. Accordingly, the reflecting mirror 76 has an outer diameter corresponding to the inner diameter of the mirror supporting member 93 or corresponding to the inner diameter of the compression rubber ring 94 set on the mirror supporting member 93.

Figure 6:
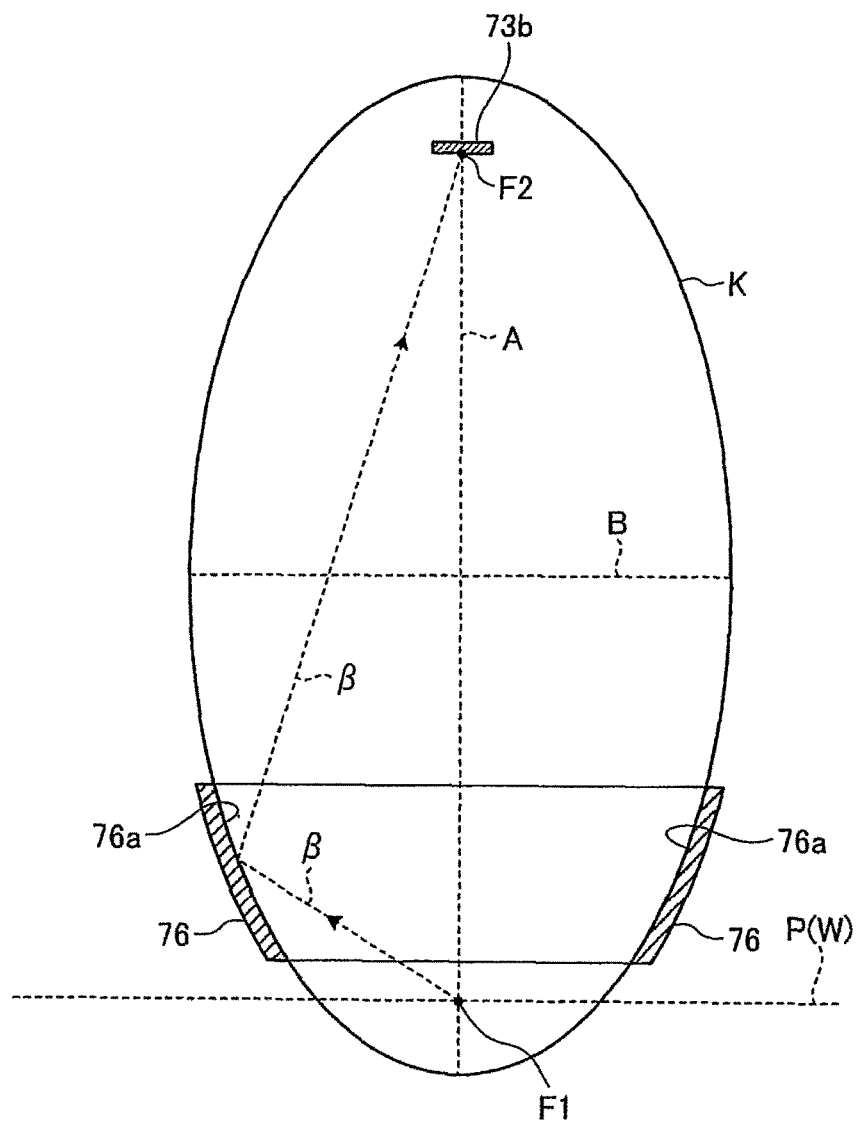
FIG. 6 is a schematic diagram showing the positions of the protective film and a light detecting element with respect to a reflecting mirror having an elliptical reflecting surface.

The inner circumferential surface of the reflecting mirror 76 is formed as a reflecting surface 76a. As shown in FIG. 6, the reflecting surface 76a is formed by a part of a curved surface forming a spheroid. The spheroid is formed by rotating an ellipse K having a major axis A extending in the vertical direction and a minor axis B perpendicular to the major axis A, wherein the ellipse K is rotated around the major axis A to thereby form the spheroid. It is known that an ellipse has two foci and that light emitted from one of the two foci is reflected on the ellipse to reach the other focus.

As shown in FIG. 6, the ellipse K forming the spheroid has two foci F1 and F2 (a first focus F1 and a second focus F2). The photomultiplier tube 73 is mounted so that the light detecting element 73b of the photomultiplier tube 73 is positioned at the second focus F2 (the other focus). On the other hand, the target area on the protective film P where the excitation light α is to be applied is positioned at the first focus F1 (one of the two foci). The fluorescence detecting unit 71 can be adjusted in vertical position with respect to the protective film P formed on the wafer W, by operating a suitable mechanism (not shown). That is, the vertical position of the fluorescence detecting unit 71 is adjusted so that the first focus F1 is positioned on the upper surface of the protective film P. In this preferred embodiment, the movable distance of the fluorescence detecting unit 71, or the spacing H between the upper surface of the protective film P on which the first focus F1 is positioned and the lower end of the fluorescence detecting unit 71 is set to 2.5 mm. In this case, the spot diameter of the excitation light α to be applied to the protective film P is 0.6 mm, for example.

With this configuration, the excitation light α is applied to the protective film P positioned at the first focus F1 as shown in FIG. 5. As a result, the fluorescence β is emitted from the absorbing agent contained in the protective film P due to the absorption of the excitation light α. This fluorescence β is reflected on the reflecting surface 76a as a part of the spheroid and then converged to the second focus F2. As a result, the fluorescence β is detected by the light detecting element 73b positioned at the second focus F2. Accordingly, the fluorescence β emitted from the absorbing agent can be efficiently guided through the reflecting surface 76a to the light detecting element 73b positioned at the second focus F2, thereby reducing a loss of feeble fluorescence. Further, since the light detecting element 73b is positioned at the second focus F2, the formed condition of the protective film P can be precisely detected by using fluorescence even having a low intensity. In addition, the detection of the protective film P on the wafer W can be performed quickly.

Further, the light source included in the excitation light applying section 75 is located outside the casing 72. Accordingly, a temperature rise (temperature variations) in the inside of the casing 72 and on the reflecting surface 76a of the reflecting mirror 76 can be suppressed, so that a strain on the reflecting surface 76a due to such a temperature rise can be suppressed and the fluorescence β can be accurately reflected toward the light detecting element 73b.

Figure 7:
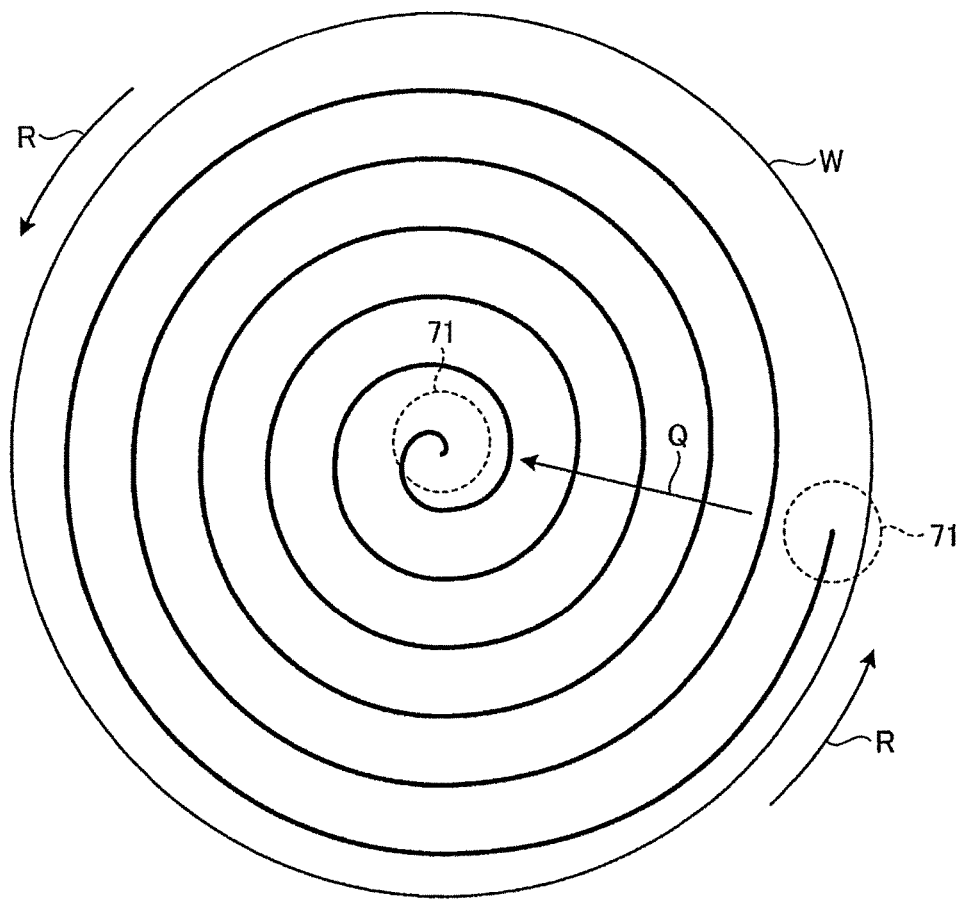
FIG. 7 is a schematic diagram showing the operation in detecting the formed condition of the protective film on the wafer by using the fluorescence detecting unit.

A specific detection method for the fluorescence will now be described. The wafer W having the protective film P is held on the chuck table 10, and the height of the fluorescence detecting unit 71 is adjusted so that the first focus F1 is positioned on the upper surface of the protective film P. In this condition, the chuck table 10 is rotated at a predetermined speed (e.g., 3000 rpm) to thereby rotate the wafer W in a predetermined direction (in the direction shown by an arrow R in FIG. 7). Thereafter, the excitation light α is continuously applied from the fluorescence detecting unit 71 toward the protective film P of the wafer W. At the same time, as shown in FIG. 7, the chuck table 10 (FIG. 1) is moved so that the fluorescence detecting unit 71 is relatively moved from the periphery of the wafer W toward the center thereof in the radial direction (in the direction shown by an arrow Q in FIG. 7). As a result, the fluorescence detecting unit 71 follows a spiral path from the periphery of the wafer W toward the center thereof.

This spiral path is called an Archimedean spiral, which is expressed as $r=a\theta$ where r is the distance from the center and $\theta$ is the rotational angle in a polar coordinate system. Further, the polar coordinates may be converted into $x=a\theta\cos\theta$ and $y=a\theta\sin\theta$. On the basis of this fact, it is assumed that the fluorescence detecting unit 71 is moved at a constant velocity. The fluorescence detecting unit 71 is started with a reference value set in a notch filter and is then moved at a constant velocity. Accordingly, by grasping the rotational angle from the start of the chuck table 10 (wafer W), the x and y positions on the wafer W can be calculated by performing the conversion from the polar coordinates. For example, assuming that the radius of the wafer W is 150 mm, that the beam size of the excitation light is 300 μm, and that the entire surface of the wafer W is subjected to the detection, the required number of rotations of the wafer W is 500, i.e., the rotational angle is 180000 degrees. In this case, the expression of the Archimedean spiral is given as $r=150\theta/180000$.

The detection of the rotational angle may be realized by using a rotary encoder, for example. Further, the timing of data acquisition may be set to the interval equal to the beam size. In performing the data acquisition, a threshold of 20000 counts, for example, is set for the detection of fluorescence. Only when the count value obtained by the rotary encoder is less than 20000 counts, this count value is read and stored as NG into a memory. In displaying the result of detection, a grid (e.g., 1-mm pitch grid) is formed on a 300-mm wafer map with a predetermined display resolution. An NG area on the wafer map where the count value is less than the threshold is colored so that the number of NGs can be seen.

In determining the formed condition of the protective film P, a binarizing technique may be applied. In the case of FIG. 7, a count value of 20000 is previously set as the threshold, and a count value corresponding to the fluorescence intensity at each position is compared with the threshold. In binarizing the fluorescence intensity on the entire surface of the wafer W, the following methods may be adopted.

(1) The correspondence between detection position and fluorescence intensity is stored into a memory, and the fluorescence intensity on the entire surface of the wafer W is then obtained. Thereafter, the fluorescence intensity obtained is compared with the threshold.

(2) Every time the fluorescence intensity is obtained at each detection position, the fluorescence intensity obtained is compared with the threshold. Further, whether or not the protective film P has been properly formed is determined according to the result of this comparison. When the protective film P is not properly formed, the corresponding detection position is stored into the memory. In this case, the amount of data to be processed is small, so that a processing speed can be increased. Further, the distribution of coated and uncoated portions of the protective film P may be prepared according to the detection positions on the entire surface of the wafer W where the protective film P has not been properly formed.

The uncoated portion where the count value is less than the threshold may be indicated by a first color, and the coated portion where the count value is greater than the threshold may be indicated by a second color different from the first color. In this case, these coated and uncoated portions differently colored may be displayed by a display section included in the laser processing apparatus 1. Further, the areas of the individual uncoated portions and the number of the individual uncoated portions may be represented by a histogram (frequency distribution chart) according to the data binarized. According to this histogram, any required next processing may be selected. For example, in the next processing, only the uncoated portions may be coated again or the protective film may be removed by cleaning to coat the entire surface of the wafer W again. In this case, when the area of each uncoated portion is large and the number of the uncoated portions is small, only the uncoated portions may be coated again. In contrast, when the area of each uncoated portion is small and the number of the uncoated portions is large, the protective film may be removed by cleaning. Further, a rate of coverage with the protective film P may be determined. When the coverage rate determined is less than a predetermined coverage rate, the wafer W may be cleaned to remove the protective film P and the liquid resin may be applied again to the entire surface of the wafer W.

In this preferred embodiment, the chuck table 10 is rotated around its axis (θ rotation) and simultaneously moved in the X direction relative to the fluorescence detecting unit 71. As a modification, the fluorescence detecting unit 71 may be moved in the X direction or in the Y direction relative to the chuck table 10. Further, while the fluorescence detecting unit 71 is relatively moved from the periphery of the wafer W toward the center thereof in the above preferred embodiment, the fluorescence detecting unit 71 may be relatively moved from the center of the wafer W toward the periphery thereof.

With the above configuration, the formed condition of the protective film P on the wafer W can be simply detected. According to the experiment by the present inventor, the formed condition of the protective film P on the wafer W having a diameter of 300 mm could be detected in a short time of approximately 30 to 40 seconds. In this case, the moving speed of the chuck table 10 is preferably decreased with the detection position approaching the periphery of the wafer W. Accordingly, even when the sampling intervals at the central portion of the wafer W are equal to that at the peripheral portion of the wafer W, sampling can be performed with a predetermined pitch of positions. The sampling intervals may be suitably selected with desired accuracy.

Figure 8:
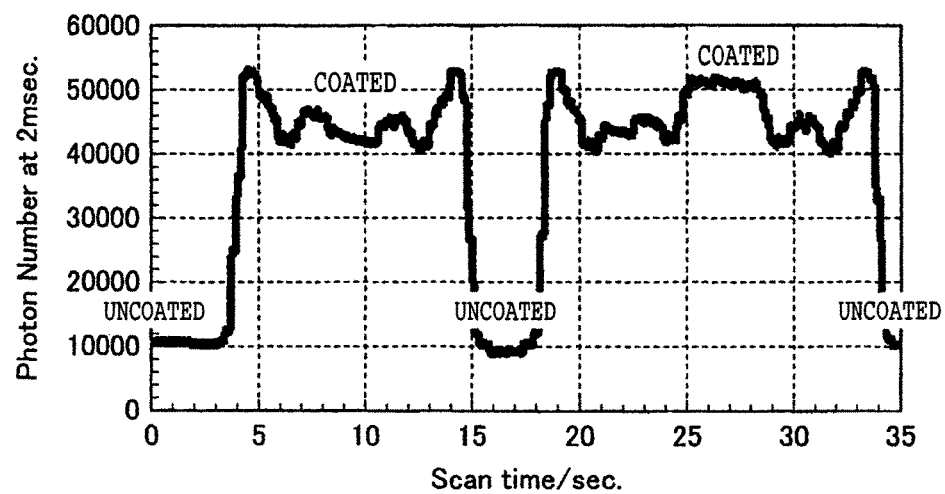
FIG. 8 is a graph showing the result of detection of the formed condition in the case that the protective film is formed on a wafer having devices on the front side.
Figure 9:
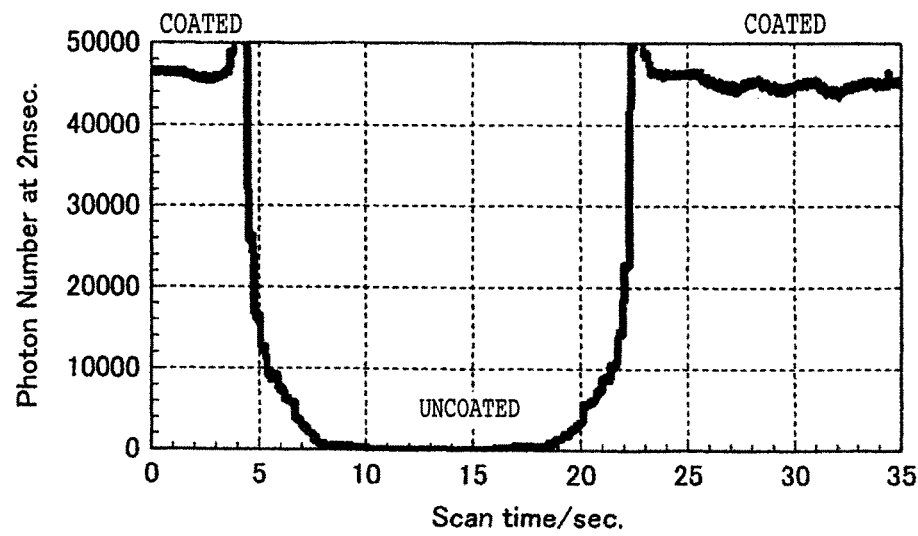
FIG. 9 is a graph showing the result of detection of the formed condition in the case that the protective film is formed on a mirror wafer of silicon.
Figure 10:
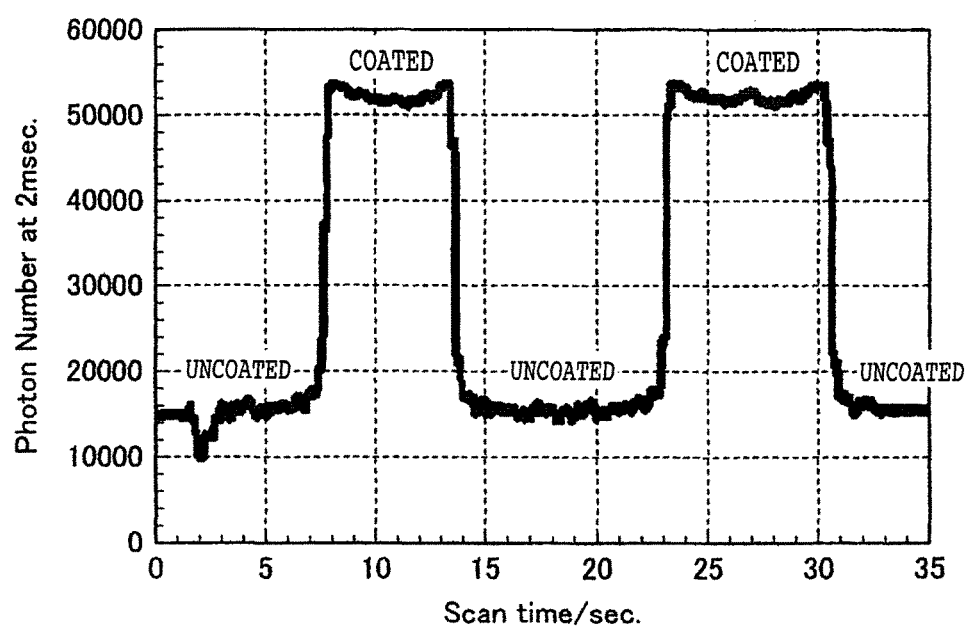
FIG. 10 is a graph showing the result of detection of the formed condition in the case that the protective film is formed on a wafer having bumps (electrodes) on the front side.

FIGS. 8 to 10 are graphs showing the results of detection of the formed condition of the protective film P by the use of the fluorescence detecting unit 71. FIG. 8 shows the formed condition detected in the case that the protective film P is formed on a wafer having devices formed on the front side. FIG. 9 shows the formed condition detected in the case that the protective film P is formed on a mirror wafer of silicon. FIG. 10 shows the formed condition detected in the case that the protective film P is formed on a wafer having bumps (electrodes) provided on the front side.

In FIGS. 8 to 10, the formed condition of the protective film P is determined according to the measured number of secondary electrons generated by the photoelectrons (photons) of the fluorescence emitted from the protective film P. As shown in FIGS. 8 to 10, the measured number of photoelectrons (photons) is large at the coated portions of the protective film P, whereas the measured number of photoelectrons (photons) is small at the uncoated portions of the protective film P. Thus, the formed condition of the protective film P can be detected with high accuracy according to the contrast between the coated portions and the uncoated portions of the protective film P.

In the case that the uncoated portions are detected due to the presence of bubbles or the like according to the result of detection of the formed condition of the protective film P, only the uncoated portions may be coated again with the liquid resin. Alternatively, the protective film P may be once removed by cleaning, and the entire surface of the wafer W may be coated again with the liquid resin.

Figure 11:
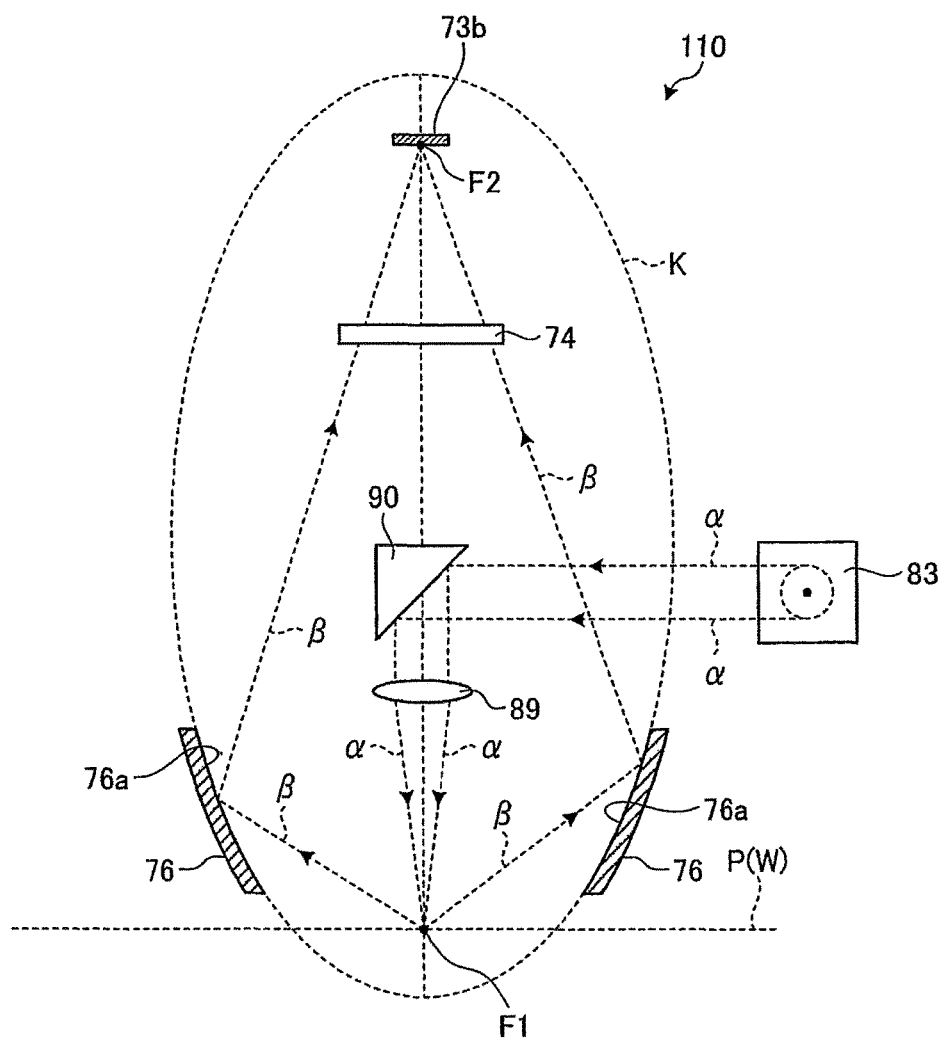
FIG. 11 is a schematic diagram showing the configuration of a fluorescence detecting unit according to a modification of the preferred embodiment.

FIG. 11 is a schematic diagram showing the configuration of a fluorescence detecting unit 110 according to a modification of the above preferred embodiment. In this modification, the same parts as those shown in FIG. 5 are denoted by the same reference symbols, and the description thereof will be omitted. While the focusing lens 89 is interposed between the first mirror 83 and the second mirror 90 in the fluorescence detecting unit 71, the focusing lens 89 in the fluorescence detecting unit 110 is interposed between the second mirror 90 and the target area of the protective film P as shown in FIG. 11.

Figure 12:
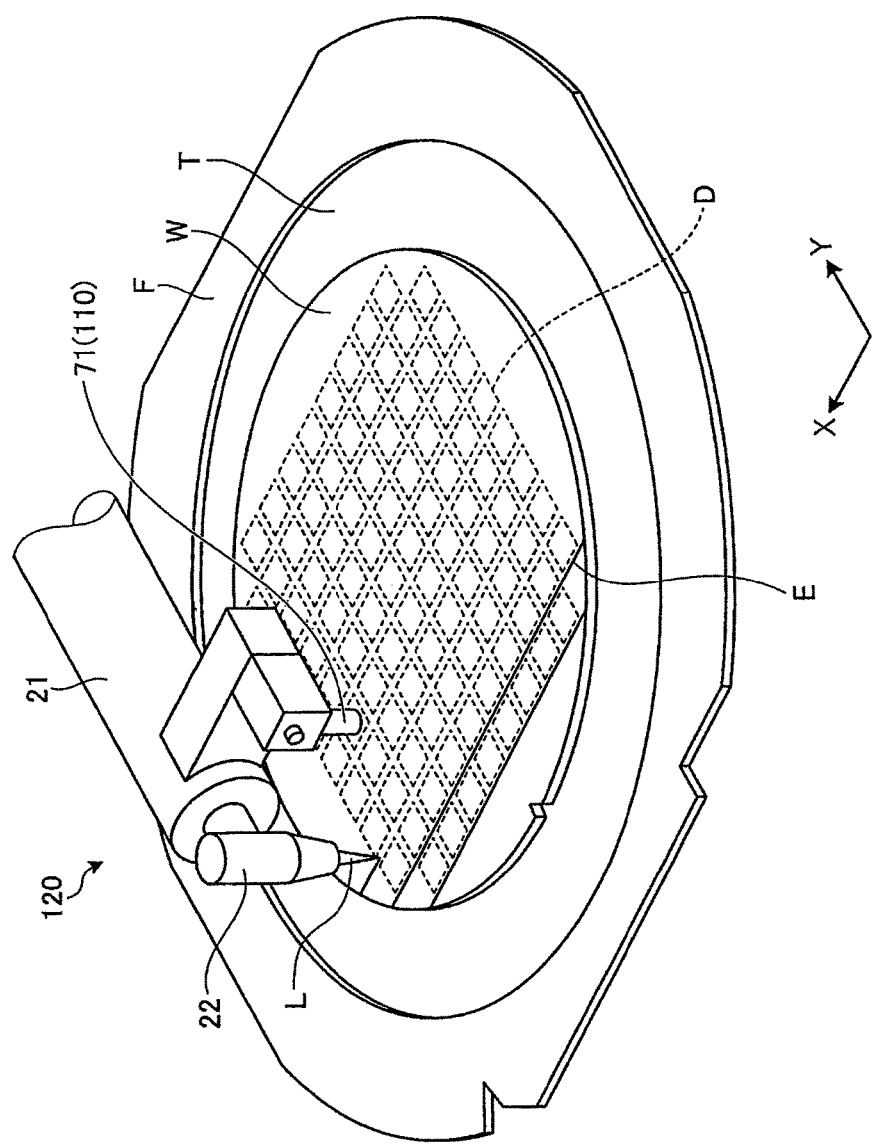
FIG. 12 is a perspective view showing another modification, wherein the fluorescence detecting unit is mounted on a laser beam applying unit.

FIG. 12 is a perspective view showing another modification, wherein the fluorescence detecting unit 71 (110) is mounted on a laser beam applying section 120. In the above preferred embodiment, the fluorescence detecting unit 71 is mounted on the support portion 3 of the body 2, the support portion 3 being formed so as to extend above the moving path of the chuck table 10. In this modification, the fluorescence detecting unit 71 (110) is mounted on the laser beam applying section 120 as shown in FIG. 12. In the configuration shown in FIG. 12, the formed condition of the protective film P (FIG. 3) cannot be detected over the entire surface of the wafer W, but can be partially detected. However, the formed condition of the protective film P can be detected along the streets L to be processed as applying a laser beam to the wafer W along the streets L to thereby form a processed groove E along each street L as shown in FIG. 12.

As another modification, the fluorescence detecting unit 71 may be movably mounted above the spinner table 51 of the coating and cleaning section 50, so as to detect the formed condition of the protective film P on the wafer W held on the spinner table 51. In this case, when the uncoated portions of the protective film P are detected, the liquid resin may be applied to only the uncoated portions or may be applied to the entire surface of the wafer W after removing the protective film P in the condition where the wafer W remains held on the spinner table 51.

Further, the formed condition of the protective film P is detected by detecting the presence or absence of the protective film P in the above preferred embodiment. As a modification, the thickness of the protective film P may be detected. For example, a predetermined number of photons corresponding to a predetermined film thickness is previously set. When the measured number of photons is greater than the predetermined number of photons, the control section 100 determines that the formed condition of the protective film P is good. In this case, a plurality of wafers W having protective films P different in thickness are prepared, and the excitation light α is applied to the wafers W (protective films P) to detect the fluorescence β for each wafer W, thereby setting the number of photons corresponding to the thickness of each protective film P (preparing step). Thereafter, the excitation light α is applied to the protective film P having an unknown thickness to detect the fluorescence β. Then, the thickness of the protective film P is estimated from the number of photons in the fluorescence β.

The present invention is not limited to the details of the above described preferred embodiment. The scope of the invention is defined by the appended claims and all changes and modifications as fall within the equivalence of the scope of the claims are therefore to be embraced by the invention.

What is claimed is:

1. A fluorescence detecting apparatus for detecting whether or not a protective film is properly formed on the front side of a workpiece, by using fluorescence emitted from said protective film, said protective film being formed to protect the front side of said workpiece from processing dust generated in applying a laser beam to the front side of said workpiece to process said workpiece, said protective film being formed of a resin containing an absorbing agent capable of absorbing said laser beam, said fluorescence detecting apparatus comprising:
a holding section configured to hold said workpiece; and
light detecting means for detecting said fluorescence emitted from said protective film to thereby detect the formed condition of said protective film;
said light detecting means including
an excitation light applying section configured to apply excitation light to said protective film, said excitation light having an absorption wavelength to said absorbing agent contained in said protective film,
a light detecting section configured to detect said fluorescence emitted from said absorbing agent due to the absorption of said excitation light,
a filter for removing light having wavelengths other than the wavelength of said fluorescence emitted from said absorbing agent, and
a reflecting mirror having a reflecting surface for reflecting said fluorescence emitted from said protective film toward said light detecting section;
said reflecting surface being formed by a part of a curved surface forming a spheroid having two foci, one of said two foci being positioned at a target area of said protective film where said excitation light is applied; whereas the other focus being positioned at said light detecting section.

2. The fluorescence detecting apparatus according to claim 1, wherein said light detecting section includes a photomultiplier tube.

3. The fluorescence detecting apparatus according to claim 1, wherein said excitation light applying section is provided between said target area of said protective film and said filter.

4. The fluorescence detecting apparatus according to claim 1, wherein said holding section is used also in performing laser processing to said workpiece.

5. The fluorescence detecting apparatus according to claim 1, wherein said light detecting means further includes a casing for storing all said excitation light applying section, said light detecting section, said filter, and said reflecting mirror.

* * * * *